United States Patent
Walton et al.

(10) Patent No.: US 8,342,027 B2
(45) Date of Patent: Jan. 1, 2013

(54) DETERMINING PHYSICAL PROPERTIES OF OBJECTS OR FLUIDS IN MULTI-PATH CLUTTER ENVIRONMENTS

(75) Inventors: Eric K. Walton, Columbus, OH (US); Yakup Bayram, Dublin, OH (US); Orbay Tuncay, Emmaus, PA (US); Bruce G. Montgomery, Glenwood, MD (US); Gary W. Bruce, Severna Park, MD (US); Douglas E. Crowe, Herdon, VA (US); Steven E. Gemeny, Finksburg, MD (US)

(73) Assignees: The Ohio State University, Columbus, OH (US); Syntonics, LLC, Columbia, MD (US)

( * ) Notice: Subject to any disclaimer, the term of this patent is extended or adjusted under 35 U.S.C. 154(b) by 28 days.

(21) Appl. No.: 13/197,465

(22) Filed: Aug. 3, 2011

(65) Prior Publication Data

US 2012/0192617 A1  Aug. 2, 2012

Related U.S. Application Data (63) Continuation-in-part of application No. 12/537,315, filed on Aug. 7, 2009, now abandoned, which is a continuation-in-part of application No. 12/330,134, filed on Dec. 8, 2008, now abandoned.

(60) Provisional application No. 61/012,186, filed on Dec. 7, 2007.

(51) Int. Cl.
*G01N 29/36* (2006.01)
(52) U.S. Cl. ............... 73/584; 73/593; 73/597; 73/609; 73/627
(58) Field of Classification Search ............ 73/584, 73/593, 597, 609, 617, 627; 310/313 R, 310/313 B, 313 D
See application file for complete search history.

(56) References Cited

U.S. PATENT DOCUMENTS

| | | | |
|---|---|---|---|
| 3,568,102 A | 3/1971 | Tseng |
| 3,886,504 A | 5/1975 | Hartmann et al. |
| 3,955,160 A | 5/1976 | Duffy |
| 3,961,290 A | 6/1976 | Moore |
| 4,342,012 A | 7/1982 | Inaba et al. |
| 4,467,235 A | 8/1984 | De Wames et al. |
| 4,870,312 A | 9/1989 | La Rosa et al. |

(Continued)

OTHER PUBLICATIONS

"Wireless Strain Gage System New Release", Syntonics, Jul. 29, 2005.

(Continued)

*Primary Examiner* — David Rogers
(74) *Attorney, Agent, or Firm* — Dinsmore & Shohl LLP (57) ABSTRACT

A method for determining a physical property of an object or fluid in a dynamic multi-path clutter environment comprises transmitting an RF interrogation signal to a wireless sensor physically coupled to the object or fluid (gas or liquid) in the dynamic multi-path clutter environment, wherein the wireless sensor is operable to receive the RF interrogation signal, produce a reference signal and a measurement signal, and retransmit the reference signal and the measurement signal in the dynamic multi-path clutter environment. The reference signal and measurement signal are delayed by the wireless sensor by an amount of time that may be a function of the unknown physical property. The method also comprises receiving the retransmitted reference signal and the retransmitted measurement signal and comparing them in the time domain in order to determine the unknown physical property of the object or fluid. The method further comprises setting the time delays of the retransmitted reference and retransmitted measurement signals to be long enough for the ringdown time to be over but not so long so that the differential time is distorted by the dynamics of the system.

20 Claims, 7 Drawing Sheets

U.S. PATENT DOCUMENTS

| | | | |
|---|---|---|---|
| 5,365,770 | A | 11/1994 | Meitzler et al. |
| 5,469,170 | A | 11/1995 | Mariani |
| 6,378,370 | B1 | 4/2002 | Haskell et al. |
| 6,788,204 | B1 | 9/2004 | Ianelli et al. |
| 6,988,026 | B2 | 1/2006 | Breed et al. |
| 7,005,964 | B2 | 2/2006 | Edmonson et al. |
| 7,071,404 | B1 | 7/2006 | Smith |
| 7,100,452 | B2 | 9/2006 | Marsh |
| 7,267,009 | B2 | 9/2007 | Liu et al. |
| 7,268,662 | B2 | 9/2007 | Hines et al. |
| 7,331,236 | B2 | 2/2008 | Smith et al. |
| 7,551,058 | B1 | 6/2009 | Johnson et al. |
| 7,764,958 | B2 | 7/2010 | Townsend et al. |
| 7,924,160 | B1 | 4/2011 | LaPenta et al. |
| 8,094,008 | B2 | 1/2012 | Solie et al. |
| 2002/0005677 | A1 | 1/2002 | Reindl et al. |
| 2003/0102984 | A1 | 6/2003 | Elsner et al. |
| 2004/0244496 | A1 | 12/2004 | Bernhard et al. |
| 2005/0264275 | A1 | 12/2005 | Bosselmann et al. |
| 2006/0025897 | A1 | 2/2006 | Shostak et al. |
| 2006/0048581 | A1 | 3/2006 | Bosselmann et al. |
| 2006/0115360 | A1 | 6/2006 | Bosselmann et al. |
| 2006/0283252 | A1 | 12/2006 | Liu et al. |
| 2007/0052516 | A1 | 3/2007 | Hines et al. |
| 2007/0064765 | A1 | 3/2007 | Solie |
| 2007/0132461 | A1 | 6/2007 | Holmquist et al. |
| 2007/0283758 | A1 | 12/2007 | Funo et al. |
| 2009/0039864 | A1 | 2/2009 | Gordon |
| 2009/0121847 | A1 | 5/2009 | Solie et al. |

OTHER PUBLICATIONS

"Wireless Strain Gage System News Release", Syntonics, Nov. 1, 2006.

Tuncay Orbay, "Wireless Strain Guage System in a Multipath Enviorment", 2008.

W.E. Bulst et al., "State of the Art in Wireless Sensing with Surface Acoustic Waves", IEEE Transactions on Industrial Electronics, vol. 48, No. 2, pp. 265-271, Apr. 2001.

Russell G. DeAnna, "Wireless Telemetry for Gas-Turbine Applications", NASA/TM-2000-209815, Mar. 2000.

Klaus Finkenzeller, "Physical Principles of RFID Systems", RFID Handbook: Fundamentals and Applications in Contactless Smart Cards and Identification 2nd Ed. Ch. 4, pp. 61-159, published 2003.

Victor Kalinin, "Passive Wireless Strain and Temperature Sensors Based on Sawa Devices", IEEE Radio and Wireless Conference, Sep. 19-22, 2004: Proceedings, pp. 187-190, 2004.

Pohl, "A Low-Cost High Definition Wireless Sensor System Utilizing Intersymbol Interface", IEEE Transactions on Ultrasonics, Ferroelectronics, and Frequency Control, vol. 45, No. 5, pp. 1355-1362, Sep. 1998.

Reindl, "Saw-Based Radio Sensor Ssytems", IEEE Sensors Journal, vol. 1, No. 1, pp. 69-78, Jun. 2001.

Thiele, et al, "High Temperature SAW Gas Sensor on Langasite", Proceedings of IEEE on Sensors, vol. 2, pp. 769-772, Oct. 2003.

Drafts, "Acoustic Wave Technology Sensors", IEEE Trans. MTT, vol. 49 No. 4, pp. 795-802, Apr. 2001.

Wolff, et al., "SAW Sensors for Harsh Environments", IEEE Sensors Journal, vol. 1 No. 1, pp. 4-13, Jun. 2001.

Reeder, et al., "Surface-Acoustic Wave Pressure and Temperature Sensors", Proceedings of IEEE, vol. 64 No. 5, pp. 754-756, May 1976.

Fachberger, et al., "Applicability of LiNbO3, Langasite and GaPO4 in High Temeratrue SAW Sensors Operating at Radio Frequencies", IEEE Trans. Ultrasonics, L. Ferroelectrics and Frequency Control, vol. 51, No. 11, Nov. 2004.

Seh et al., "Langasite for High Temperature Acoustic Wave Gas Sensors", Sensors and Actuators B 93, pp. 169-174, 2003.

Penza, et al., "Carbon nanotubes as SAW chemical sensors materials", Sensors and Actuators B, pp. 47-59, Feb. 2004.

Reindl, et al., "Theory and Application of Passive SAW Radio Transponders as Sensors", IEEE Transactions on Ultrasonics, Ferroelectrics, and Frequency Control, vol. 45, No. 5, pp. 1281-1292, Sep. 1998.

Reindl, et al., "SAW Devices as Wireless Passive Sensors", IEEE Ultrasonics Symposium, pp. 363-367, 1996.

Scholl, et al., "Wireless Passive Saw Sensor Systems for Industrial and Domestic Applications", IEEE International Frequency Control Symposium, pp. 595-601, 1998.

Scholl, et al, "Wireless Passive Saw Sensor Systems for Industrial and Domestic Applications", IEEE International Frequency Control Symposium, pp. 595-601, 1998.

Pohl, "A Review of Wireless SAW Sensors", IEEE Transactions on Ultrasonics, Ferroelectrics, and Frequency Control, vol. 47, No. 2, pp. 317-332, Mar. 2000.

Grossmann, et al., "Measure of Mechanical Quantities Using Quartz Sensors", European Frequency Time Forum, Mar. 5-7, 1996 Conference Publication No. 418 IEE, pp. 376-381, 1996.

Varadan, et al., "Wireless passive IDT strain microsensor", Smart Mater. Struct 6, pp. 745-751, 1997.

Walton et al., "EM Propogation Inside Jet Engine Turbines", Proceedings of Antenna Measurement Techniques Association Symposium, Oct. 2006.

Walton et al., "Estimating the Time-Delay and Frequency Decay Parameter of Scattering Components using a Modified MUSIC Algorithm", IEEE Transactions on Antennas and Propogation, vol. 42, No. 10, pp. 1412-1419, Oct. 1994.

DETERMINING PHYSICAL PROPERTIES OF OBJECTS OR FLUIDS IN MULTI-PATH CLUTTER ENVIRONMENTS

CROSS-REFERENCE TO RELATED APPLICATIONS

This continuation-in-part patent application claims priority to application Ser. No. 12/537,315, filed Aug. 7, 2009, which is a continuation-in-part of non-provisional patent application Ser. No. 12/330,134, filed Dec. 8, 2008, now abandoned, which claims priority to provisional Patent Application Ser. No. 61/012,186, filed Dec. 7, 2007.

STATEMENT REGARDING FEDERALLY SPONSORED RESEARCH OR DEVELOPMENT

This invention was made with government support under Contract No. FA9550-065-C-0157 awarded by Air Force Office of Scientific Research/PKC. The Government has certain rights in this invention.

BACKGROUND

The present invention relates generally to measuring the physical properties of objects or fluids and, more particularly, to methods and sensors for determining the physical properties of objects or fluids in multi-path clutter environments. For the purposes of defining and describing the invention, it is noted that a "fluid" should be taken to define any matter with fluidic properties including, but not limited to, a gas, a liquid, a vapor, etc.

It is often necessary to measure physical properties such as temperature, strain, pressure, etc. using a wireless system. In some cases, there are a large number of multiple reflections (multi-path signal propagation environment) of the radio signals along the propagation path so that the signal to or from the sensor will be corrupted and/or modulated by the multi-path environment. When there is a number of varying coherent signal reflections along the propagation path, the result is multi-path induced variations in the phase, amplitude, and/or time domain character of the signal. This situation presents a very serious problem for sensor system design. Also, practical constraints on sensor placement, weight, size, temperature, and lifetime requirements present problems to engineers in the design of very small and light weight sensors that can operate wirelessly without a source of power.

For the purposes of describing and defining the present invention, it is noted that the term "multi-path clutter environment" refers to an environment in which electromagnetic waves are transmitted and received in the presence of reflecting structures. These reflecting structures may be stationary or may be moving within or through the environment. The reflecting structures are capable of reflecting the electromagnetic waves such that an electromagnetic wave sent through this environment may be reflected off one or more reflecting structures before reaching its intended destination. As a result of these reflections, the amplitude, phase, and/or time delay of a transmitted electromagnetic wave may be altered by the time it reaches its intended destination. Furthermore, since the reflecting structures may be moving within or through the environment, the particular reflections experienced by individual electromagnetic waves may vary in an unpredictable manner.

For the purposes of describing and defining the present invention, it is noted that the term "radio frequency signal" is an electromagnetic wave having a frequency of 1 Megahertz or higher. The term "radio frequency" may be abbreviated as "RF."

For the purposes of describing and defining the present invention, it is noted that the term "ringdown" is utilized herein to refer to the process of the energy decay of an RF signal in a multi-path clutter environment. Similarly, "multi-path ringdown time" refers to the time required for the multiple reflections of a RF signal in a multi-path environment to decay to a low enough value to be statistically or empirically insignificant. For example, the multi-path ringdown time may be defined as the amount of time necessary for the reflected RF signals to decay to an amplitude of 10% or less of the original RF interrogation signal. Other means of defining this time may be used, as is known in the art.

For the purposes of describing and defining the present invention, the term "wireless sensor" refers generally to a sensor which is capable of measuring a physical property of an object or fluid and transmitting information relating to that measurement to another device without the use of conductors or "wires." The wireless sensor itself, however, may have conductors or wires which are used to internally connect the individual components of the sensor. Furthermore, the wireless sensor may lack an internal power source, such as a battery. Instead, the energy necessary to perform a measurement may be wirelessly transmitted to the wireless sensor via electromagnetic waves (e.g., RF signals).

BRIEF SUMMARY

According to one embodiment of the invention, a method for determining an unknown physical property of an object or fluid in a dynamic multi-path clutter environment is provided. According to the method, an RF interrogation signal is transmitted to a wireless sensor physically coupled to the object or the fluid in the dynamic multi-path clutter environment. A retransmitted reference signal and a retransmitted measurement signal are subsequently received from the wireless sensor. The structure of the wireless sensor is such that, upon receipt of the RF interrogation signal, the wireless sensor produces a reference signal and a measurement signal and retransmits the reference signal and the measurement signal in the dynamic multi-path clutter environment. The retransmitted reference signal is delayed by a first time delay that may or may not be a function of the unknown physical property, while the retransmitted measurement signal is delayed by a second time delay that is a function of the unknown physical property. The retransmitted reference and measurement signals are compared to determine the unknown physical property of the object or fluid.

The first and second time delays are associated by a known relationship defined by the wireless sensor and are each long enough to permit retransmission of the reference and measurement signals without substantial overlap in time with the multipath ringdown signals generated by the RF interrogation signal. Further, the first and second time delays are such that a time period between retransmission of the reference signal and the measurement signal is sufficiently short to minimize data burst calibration errors due to the dynamics of the multi-path clutter environment. Each of these aspects of the present disclosure is described in further detail herein.

A system for determining an unknown physical property of an object or a fluid in a dynamic multi-path clutter environment is also contemplated.

BRIEF DESCRIPTION OF THE SEVERAL VIEWS OF THE DRAWINGS

The following detailed description of specific embodiments of the present invention can be best understood when read in conjunction with the following drawings, where like structure is indicated with like reference numerals and in which.

DETAILED DESCRIPTION

Figure 1:
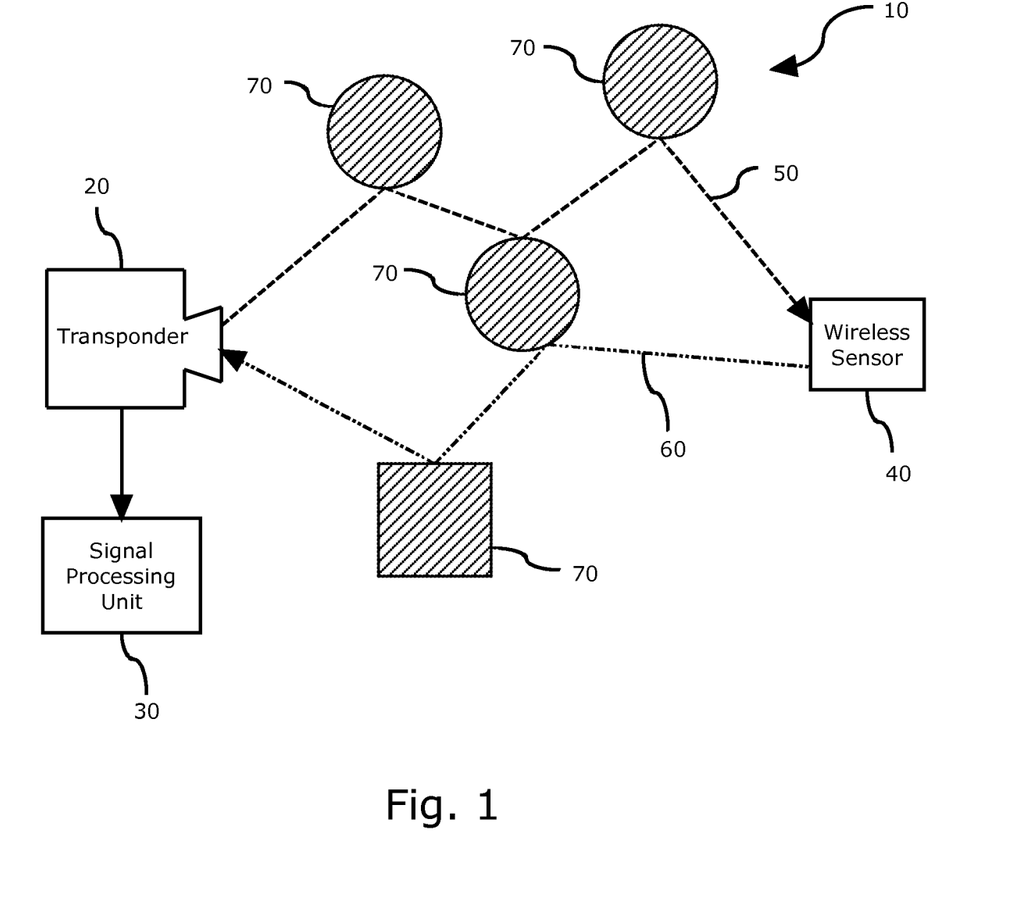
FIG. 1 depicts a representation of the wireless sensor system according to one or more embodiments described herein.

FIG. 1 depicts a wireless sensor system 10 which may operate in a multi-path clutter environment. The wireless sensor system 10 may comprise a transponder 20, a signal processing unit 30, and a wireless sensor 40. The multi-path clutter environment may comprise a plurality of reflecting structures 70, which are operable to reflect electromagnetic signals transmitted within the environment. The reflecting structures may be stationary with respect to the wireless sensor, in which case the environment may be called a "static multi-path clutter environment." In addition, at least one of the reflecting structures may be moving within or through the environment, in which case the environment may be called a "dynamic multi-path clutter environment." The embodiments of the methods and system described herein may operate in either a static or a dynamic multi-path clutter environment.

As shown in FIG. 1, the reflecting structures 70 may assume a number of different shapes. In addition, the reflecting structures 70 may comprise a number of different materials, and any single structure may comprise multiple materials. If a reflecting structure 70 is stationary, its position within the environment may be known and/or may be random. If a reflecting structure 70 is moving within or through the environment, the movement may be constant, periodic, random, etc. An individual reflecting structure 70 may move independently of the other reflecting structures or may move in a dependent fashion. Furthermore, the movement of the reflecting structure 70 may be in any axis of motion, both linear and rotational motion. In summary, it is contemplated that the reflecting structures 70, if moving within the environment, may move in any direction at any time.

Continuing to refer to FIG. 1, the transponder 20 is operable to transmit a wireless RF interrogation signal 50 to the wireless sensor 40 in the multi-path clutter environment. The RF interrogation signal 50 may reflect off of several reflecting structures 70 before reaching the wireless sensor 40. The specific path illustrated in FIG. 1 is simplified for clarity and merely represents a single RF interrogation pulse. There will typically be multiple different paths an RF signal pulse can take in a particular environment depending on the physical arrangement of the reflecting structures at the instant of time that the RF interrogation signal 50 is transmitted. The transponder receives wireless signals retransmitted by the wireless sensor 40 in the multi-path clutter environment. Return signals 60 retransmitted by the wireless sensor 40 to the transponder 20 may also be reflected by the reflecting structures 70 along a variety of return paths depending on the physical arrangement of the reflecting structures and the instant of time the return signal 60 is retransmitted. As is indicated schematically in FIG. 1, the RF interrogation signal 50 and the return signal 60 may take completely independent paths and may reflect off different reflecting structures 70.

The wireless sensor 40, which may be moving very rapidly relative to the transponder 20 (i.e., with peak velocities exceeding 1,000 feet per second), is operable to receive the RF interrogation signal 50 transmitted by the transponder 20, produce a reference signal and a measurement signal, and retransmit the reference signal and the measurement signal to the transponder in the multi-path clutter environment. In FIG. 1, the reference signal and the measurement signal are both represented by the return signal 60. The reference signal and the measure signal may take the same path before being received by the transponder 20. Like the RF interrogation signal 50, the reference signal and the measurement signal will likely reflect off a plurality of reflecting structures 70 before reaching the transponder 20.

The wireless sensor 40 is operable to produce the reference signal and the measurement signal, both of which are derived from the RF interrogation signal 50. As will be described in detail below, the reference signal is delayed by a first time delay that is optionally a function of the physical property to be determined, and the measurement signal is delayed by a second time delay that is a function of the physical property to be determined. The use of two delayed reflections from the SAW device permits the induced variations in the propagation environment to be cancelled, and the corresponding physical property to be derived. The time delays of the two reflected signals are detected by the transponder 20 and measured at the signal processing unit 30. This measurement may then be used to estimate the value of the physical property.

By incorporating the first and second time delays into the system and methodology of the present disclosure, those practicing the concepts of the present disclosure can effectively design the wireless sensor 40 so that it avoids data burst overlap due to ringdown and data burst calibration problems due to the dynamics of the dynamic propagation environment. More specifically, the present inventors have recognized that wireless sensors contemplated herein should be designed to account for the ringdown time and the system time dynamics. The ringdown time is the time required for nearly all of the multiple internal reflections from the environment to die down after the transmitted signal burst of the RF interrogation signal is turned off. Recognizing that the returned signals should not overlap in time with the multipath ringdown signals from the transmit burst, the present disclosure contemplates that the wireless sensor 40 should be designed so that the two data signals do not overlap each other. In addition, the present disclosure contemplates that the wireless sensor 40 should be designed so that the two data signals are close enough in time so that the dynamic multipath system does not change significantly during the time between these two signals.

As an illustrative example of an environment where there is significant multipath reflections in a dynamic environment, consider the inside of a jet engine. An example of the measurement of ringdown time in such an environment can be found in a paper presented at the 2006 Antenna Measurement Techniques Meeting on Oct. 22-27, 2006 in Austin, Tex. ("EM PROPAGATION IN JET ENGINE TURBINES," by Eric Walton, Jonathan Young, Jim Moore and Kyle Davis of The Ohio State University ElectroScience Laboratory). Generally, the present inventors have recognized that, upon transmission of an RF interrogation burst in a jet engine, there will be a relatively strong response that increases and then falls off in time. In the illustrated example, after approximately 20 ns from the initial response, the received signal level has fallen off to the average background level. Accordingly, the ringdown time is approximately 20 ns and, practicing the concepts of the present disclosure, the delay time to the first returned signal from the wireless sensor 40, i.e. the retransmitted reference signal, is delayed by at least 20 ns. Further, the spacing between subsequent response pulses should also be larger than 20 ns. Of course, other multipath environments will have different ringdown times that can be determined in this way. It is also contemplated that ringdown time may be determined in a variety of alternative ways. Indeed, any method that provides a measure of the time for the various internal reflections from the multipath environment to drop to a level approximating background noise can be used.

According to another aspect of the present disclosure, the wireless sensor is designed so that the retransmitted reference and measurement signals are so close together that the dynamic propagation environment does not change significantly between these pulses. As an illustrative example, consider the rotation rate of a jet engine to be 20,000 rpm, i.e., approximately 330 revolutions per second, or 3 milliseconds per revolution. If there are, for example fifty blades in an engine stage, then we have 3/50 milliseconds per blade passage or 60 microseconds per blade passage. If we consider that a movement of 1/60 of a blade passage, which is equal to 1 microsecond in this example, does not significantly change the propagation environment, then we can see that the pulses must be closer than 1 µs (1,000 ns) in time so that the propagation environment does not change significantly between or among the pulses returned from the wireless sensor 40. So, in this illustrative example, we can see that the wireless sensor 40 must be designed to give signal delay times greater than the ringdown time of 20 ns to avoid pulse overlap but less than 1,000 ns to avoid calibration problems associated with individual pulses being influenced by the change in the propagation environment between such pulses. Similar computations must be used in the design of wireless sensors to be used in other types of dynamic multipath environments.

Note that the signals can be thought of as short bursts of a microwave signal, or a "pulse" of signal. It is known in the art that other waveforms (such as frequency modulated continuous wave (FMCW or so called "chirp" signals), coded sequences, random or pseudorandom waveforms, etc.) may be used to achieve a similar result. We will use the term "pulse" here for simplicity of explanation.

The signal processing unit 30 may be electrically coupled to the transponder 20 and is operable to compare the reference signal and the measurement signal in the time domain and, using this comparison, determine the physical property of the object. In one embodiment, the comparison may include measuring the time difference between the reference signal and the measurement signal. In another embodiment, the comparison may involve taking the ratio of the time delay of each signal. Other methods of making the comparison in the time domain may be known to those skilled in the art.

Figure 2A:
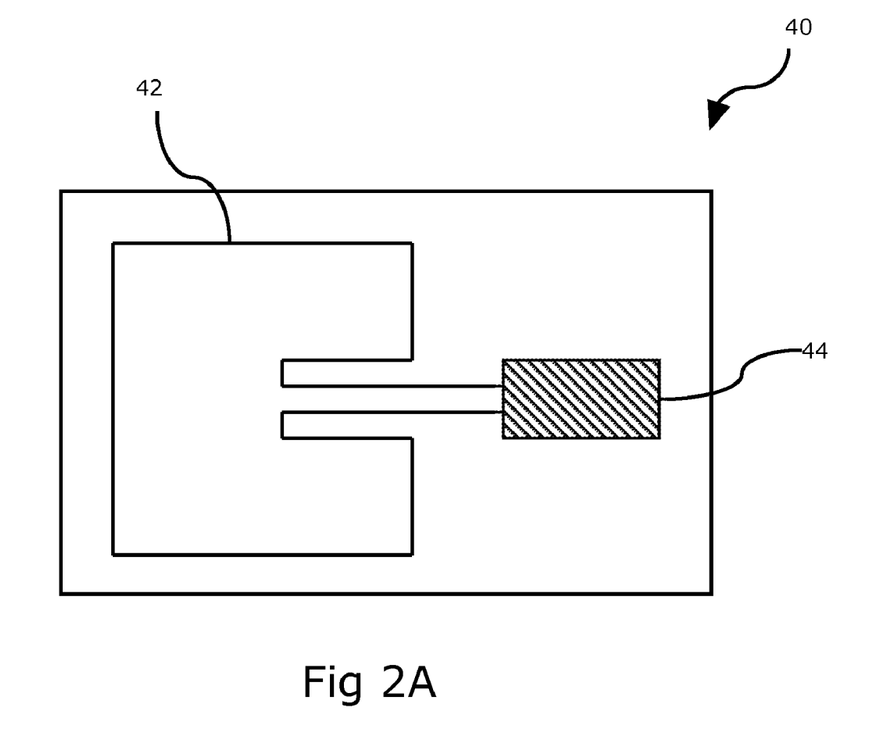
FIGS. 2A and 2B depict a wireless sensor according to one or more embodiments described herein.
Figure 2B:
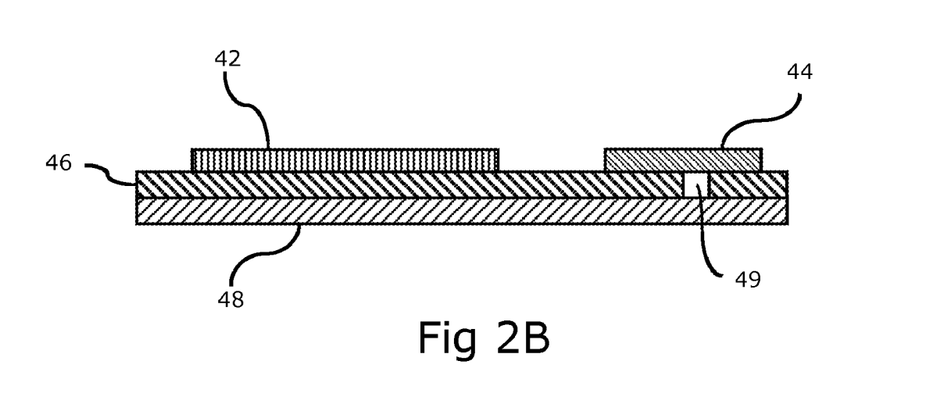

FIGS. 2A and 2B depict an exemplary wireless sensor. In this embodiment, the wireless sensor 40 comprises a patch antenna 42 electrically coupled to a surface acoustic wave ("SAW") device 44. The patch antenna 42 is operable to receive and send wireless signals, and it is electrically coupled to the SAW device 44. Other types of antennae may be used instead of a patch antenna 42, as is known in the art. FIG. 2B shows a side view of one embodiment of a wireless sensor 40. The sensor may be of a layered construction, with the patch antenna 42 and the SAW device 44 on the top, a dielectric layer 46 in the middle, and a ground plane 48 on the bottom. The SAW device may be in electrical communication with the patch antenna 42. The SAW device may also be in electrical communication with the ground plane 48 through a plated through hole 49, which passes through the dielectric layer 46. The entire sensor package including the SAW device and the antenna may be made with a thickness of less than 0.1 mm. Other types of sensor embodiments are contemplated, including sensors with different geometries, as may be found in the art or yet to be discovered. For example, the configuration of FIG. 2 is well suited for determining an unknown physical property of a gas, as the SAW device 44 is positioned on the top of the sensor. In cases where an unknown physical property of a structural component is to be determined, it would likely be more appropriate to establish the structural component as the ground plane 48 and place the SAW device 44 in more direct contact with the structural component, e.g., by placing the SAW device 44 in the same device layer as the dielectric layer 46.

It is contemplated that a single wireless sensor according to the present disclosure may have two or more SAW devices. The SAW devices may be placed in a suitable location on the wireless sensor. In wireless sensors having two or more SAW devices, each SAW device may be operable to measure either the same or a peripheral physical property. For example, a wireless sensor may have two SAW devices, each of which may be operable to measure the same physical property, such as temperature. In this case, the two temperature measurements may allow the overall system to determine the temperature gradient of the object or fluid. Furthermore, each of the SAW devices may measure a different physical property, in which case a single wireless sensor may be operable to measure, for example, temperature (e.g., a physical property) and pressure (e.g., a peripheral physical property). Other configurations which employ multiple SAW devices are contemplated. The time delays associated with the reference and measurement signal of each SAW device may be such that the measuring system is capable of distinguishing these signals. As an example, in a wireless sensor having two SAW devices, the signal delays for one SAW device may be approximately 100 nanoseconds, while the signal delays for the other SAW device may be approximately 150 nanoseconds. In this fashion, the measuring system may be able to distinguish which reference/measurement signal pair is being generated by each SAW device.

Figure 3:
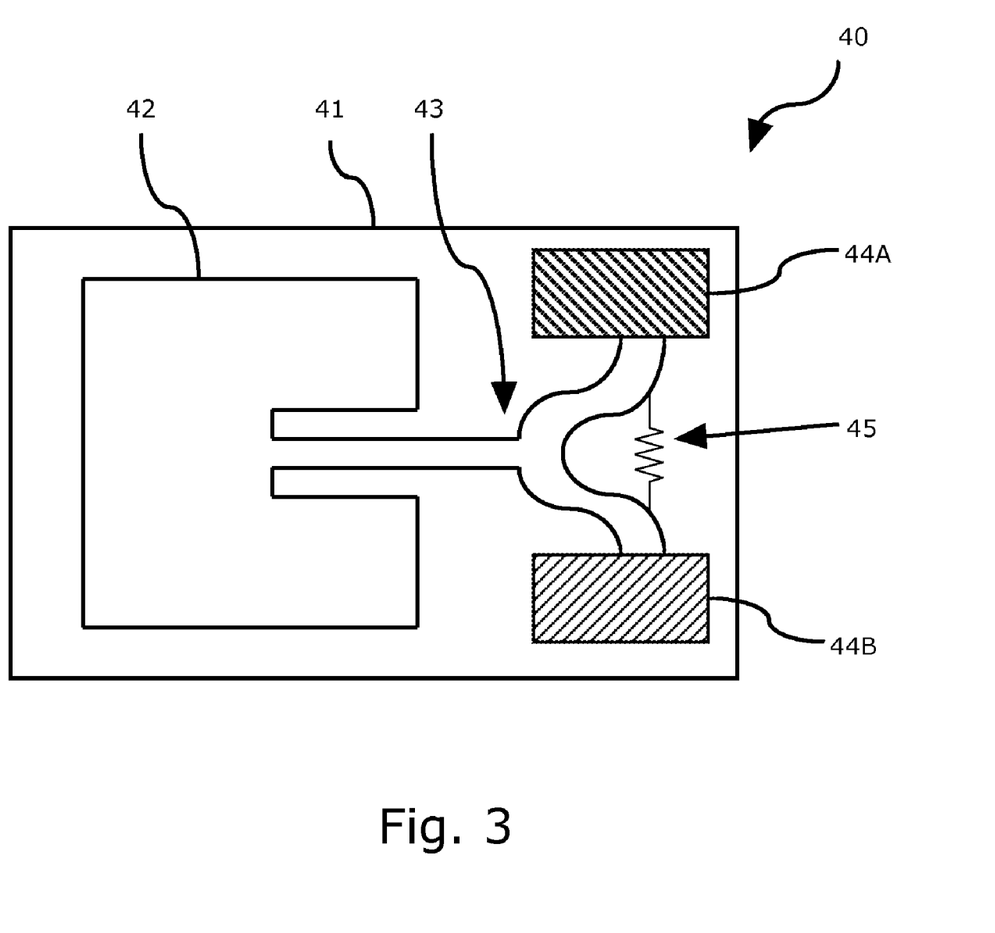
FIG. 3 depicts a wireless sensor according to one or more embodiments described herein.

FIG. 3 depicts an alternative embodiment of the wireless sensor 40 in which two SAW devices 44A, 44B are used. The wireless sensor 40 may comprise a patch antenna 42, a power divider 43, an isolating resistor 45, and two SAW devices 44A, 44B. The patch antenna 42, power divider 43, isolating resistor 45, and two SAW devices 44A, 44B may be mechanically coupled to a base 41 when configuring the sensor 40 for determining the physical properties of a fluid in the vicinity of the sensor. It is also contemplated that the base 41 may be physically coupled to an object, where a physical property of the object is of interest, although direct coupling of the SAW devices 44A, 44B to the object may be more effective. The patch antenna 42 is operable to receive the RF interrogation signal and communicate it to the power divider 43. The power divider 43 is operable to divide the RF interrogation signal and communicate a portion of it to each SAW device 44A, 44B. Each of the two SAW devices 44A, 44B is operable to receive the RF interrogation signal and produce its own reference/measurement signal pair. Each reference/measurement pair is communicated to the power divider 43 which then communicates these signals to the patch antenna 42. The patch antenna 42 is operable to receive these signals from the power divider 43 and retransmit these signals in the multipath clutter environment. The isolating resistor 45 may help isolate the signals produced by the SAW devices 44A, 44B from each other. Each of the two SAW devices 44A, 44B may be configured to measure the same physical property (e.g., a gradient of the physical property) or different physical properties, as previously discussed herein.

Figure 4:
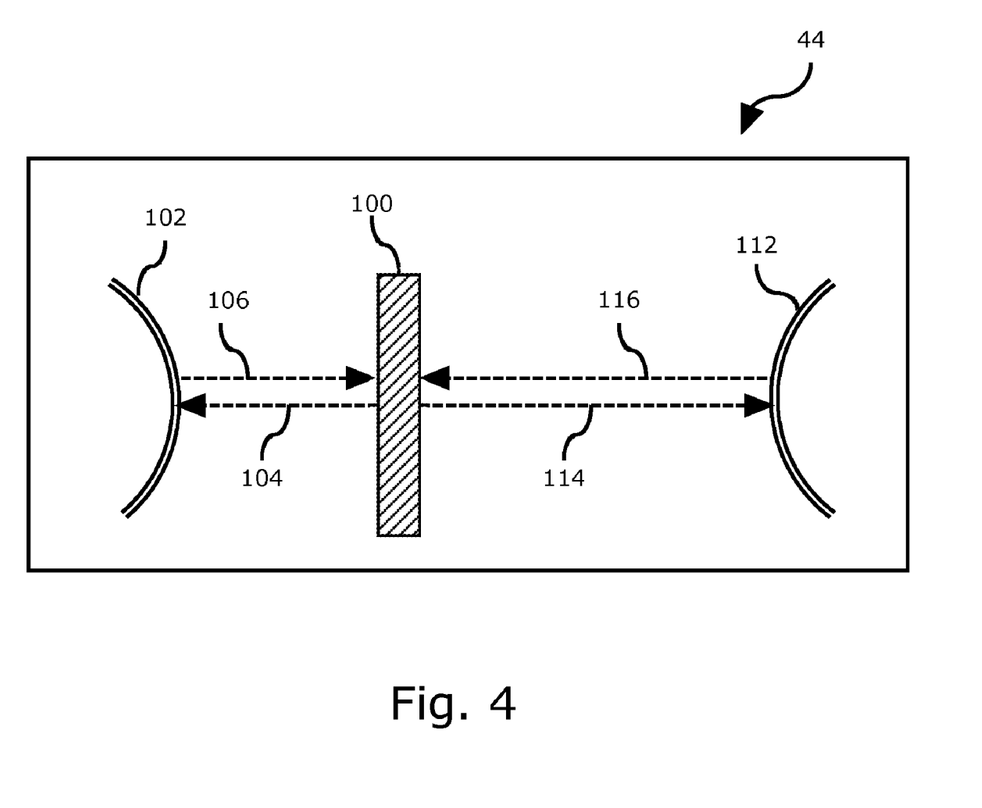
FIG. 4 depicts a SAW device according to one or more embodiments described herein.

FIG. 4 depicts an exemplary SAW device 44 according to one embodiment. The use of SAW devices as temperature and strain sensors is generally known in the art. A SAW device may comprise a piezoelectric crystal structure that is driven with a transducer, commonly referred to as an interdigital structure 100. The result is that the RF interrogation signal received by the interdigital structure 100 is converted to an acoustic signal whose velocity of propagation may be approximately 10,000 times slower (and thus the time delay is 10,000 times longer) than an electromagnetic wave in free space. The acoustic waves travel in at least two directions away from the interdigital structure 100. One acoustic wave, the incipient reference wave 104, travels from the interdigital structure 100 toward the reference reflector 102. The incipient reference wave 104 reflects off the reference reflector 102 and becomes the reflected reference wave 106. The reflected reference wave 106 travels back to the interdigital structure 100 and is converted back to an electromagnetic signal which is retransmitted by the patch antenna. In a like fashion, a second acoustic wave, called the incipient measurement wave 114, travels from the interdigital structure 100 toward the measurement reflector 112. The incipient measurement wave 114 reflects off the measurement reflector 112 and becomes the reflected measurement wave 116. The reflected measurement wave 116 travels back to the interdigital structure 100 and is converted back to an electromagnetic signal which is transmitted by the patch antenna. Although both reflectors 102, 112 are shown as arcs, it is contemplated that they may take any suitable geometric shape, such as a straight line, as is known in the art.

As discussed above, because the acoustic wave is much slower than an electromagnetic wave in space, both reflected reference waves 104, 106 and both measurement waves 114, 116 are delayed by an amount of time equal to the travel time of the waves through the piezoelectric crystal structure. Furthermore, since the reference reflector 102 and the measurement reflector 112 are located at different distances from the interdigital structure 100, the amount of time required for the reference wave to travel is different than the amount of time required for the measurement wave to travel. As a result, when the waves are converted back to electromagnetic signals by the interdigital structure and retransmitted by the patch antenna, the retransmitted reference signal and the retransmitted measurement signal are separated in the time domain. These two delays may be associated by a known relationship which is defined by the SAW device.

The physical property (e.g., strain or temperature) of the object or fluid to be measured may induce a variation in the SAW device that results in small changes in the time delay of the waves reflected back from the SAW device. As an illustrative example, an increase in the temperature of the SAW device corresponding to an increase in temperature of the object or fluid being measured may cause the propagation time of the reference waves and/or measurement waves in the SAW device to either increase or decrease. This change in the propagation time may be due to thermal expansion/contraction or crystal structure changes associated with the temperature change. As a result, the reference signal and the measurement signal retransmitted by the patch antenna of the wireless sensor will also change a corresponding amount in the time domain. This change can be captured by the transponder and measured by the signal processing unit, thus determining the temperature of the object or fluid.

Although FIG. 4 indicates that the SAW device may produce one reference and one measurement signal, it is contemplated that a single SAW device may produce multiple reference and measurement signals. In FIG. 4, the reference reflector 102 and the measurement reflector 112 permit a single physical property to be measured. However, a single SAW device may have multiple reference reflectors and multiple measurement reflectors. As such, each reference/measurement reflector pair may be operable to measure either the same or different physical properties. For example, if a SAW device has two pairs of reference/measurement reflectors, each of the two pairs may be operable to measure the same physical property, such as temperature. In such a case, one pair may measure the temperature at one part of the SAW device while the other pair may measure the temperature at another part of the SAW device. This type of arrangement may allow the gradient of the temperature to be measured with a single SAW device and may permit the measuring system to determine the direction and/or the amount of heat flow in an object or fluid. Other types of gradients may be measured as well, including but not limited to mechanical strain and pressure.

Similarly, a single SAW device with multiple reference/measurement reflectors may be operable to measure two or more different physical properties. For example, if a SAW device has two pairs of reference/measurement reflectors, one of the two pairs may be operable to measure temperature, while the other pair may be operable to measure mechanical strain. Thus, the temperature and strain of a turbine blade may be measured by a single wireless sensor. Furthermore, this type of sensor may be operable to measure physical properties from two or more objects or fluids. In another example, a SAW device having two pairs of reference/measurement reflectors may be mounted to a turbine blade in which one reference/measurement pair operates to measure the mechanical strain on the turbine blade itself, while the other reference/measurement pair operates to measure the oxygen content of the gas flowing by the turbine blade. Other combinations of physical properties may be measures as is known in the art.

Figure 5A:
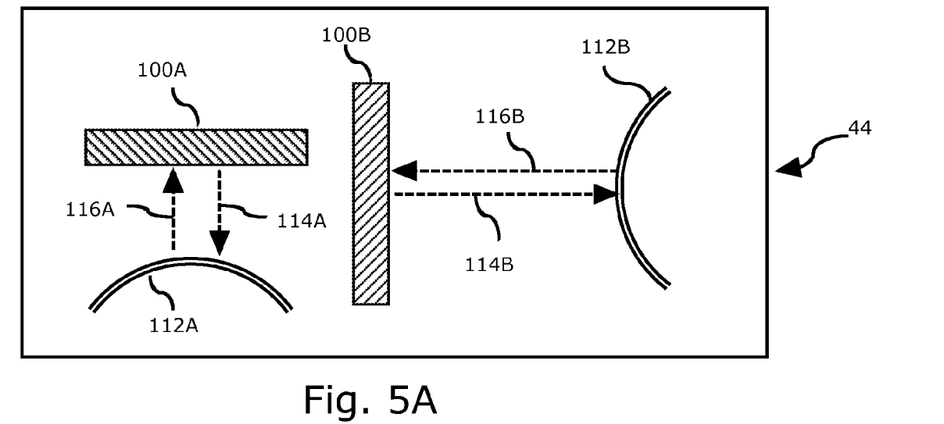
FIGS. 5A-C depict SAW devices according to one or more embodiments described herein.
Figure 5B:
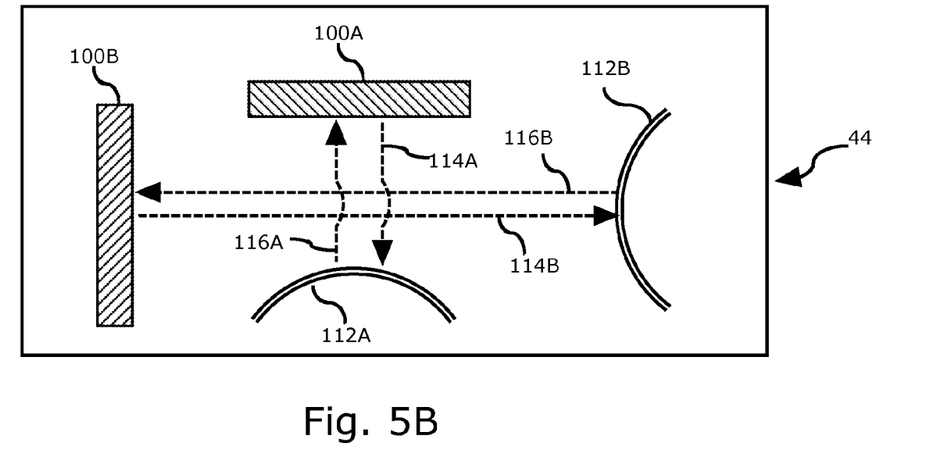
Figure 5C:
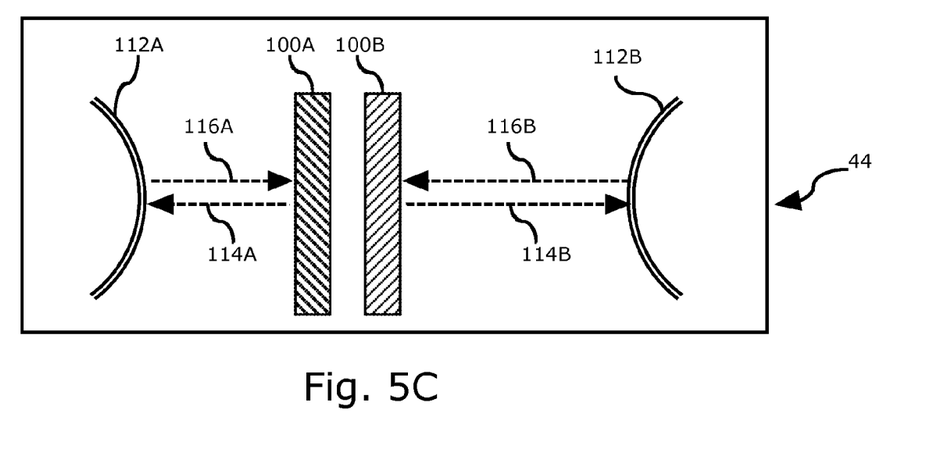

FIGS. 5A-C depict several embodiments of the SAW device 44 which may have two or more interdigital structures as well as two or more reflectors. In FIGS. 5A-C, the SAW device 44 may have two interdigital structures 100A, 100B and two corresponding measurement reflectors 112A, 112B. Each interdigital structure 100A, 100B may send out an incipient measurement wave 114B which is reflected off the measurement reflectors 112A, 112B and returns to the interdigital structures 100A, 100B as a reflected measurement wave 116B. As shown in FIGS. 5A-B, the location of the interdigital structures 100A, 100B and the measurement reflectors 112A, 112B may permit the incipient measurement waves 114A, 114B and the reflected measurement waves 116A, 116B to travel at approximately a 90-degree angle to each other. Other angles are contemplated as well. This arrangement may permit the SAW device (and the corresponding wireless sensor) to measure the gradient or the direction of a physical property of an object or a fluid. In another embodiment, the SAW devices 44 of FIGS. 5A-B may have one reference reflector and one measurement reflector, instead of the two measurement reflectors 112A, 112B as shown. This may also permit the SAW device to measure the gradient or the direction of a physical property of an object or fluid.

In FIG. 5C, the location of the interdigital structures 100A, 100B and the measurement reflectors 112A, 112B may permit the incipient measurement waves 114A, 114B and the reflected measurement waves 116A, 116B to travel at approximately along the same axis, although at physically different locations of the SAW device 44. It is also contemplated that the wave pairs may travel at some angle (other than zero) with respect to each other. This arrangement may permit the SAW device (and the corresponding wireless sensor) to measure the gradient of a physical property of an object or a fluid. Other arrangements of the reflectors (either reference and/or measurement reflectors) may be used as is known in the art or yet to be developed. Although the reflectors 112A, 112B are shown as arcs, it is contemplated that they may take any suitable geometric shape, such as a straight line, as is known in the art.

Figure 6:
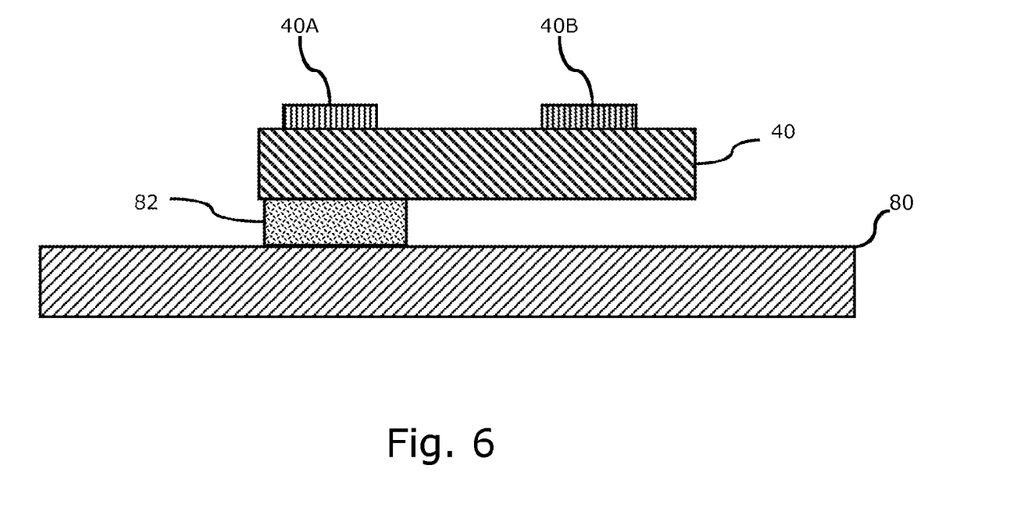
FIG. 6 depicts a wireless sensor according to one or more embodiments described herein.

FIG. 6 illustrates one embodiment of a wireless sensor 40 which is attached to an object 80 by an adhesive 82. The wireless sensor 40 has an area 40A which is operable to measure one physical property and a second area 40B which is operable to measure another physical property. In this embodiment, the adhesive 82 is located directly below the first area 40A, while no adhesive is placed beneath the second area 40B. As such, the first area 40A of the wireless sensor 40 may be operable to measure a physical property of the object 80, while the second area 40B may be operable to measure a physical property of either the object 80 or a fluid coupled to the wireless sensor in this second area 40B. In another embodiment as shown by FIG. 6, the first area 40A may be operable to measure the strain of the object 80 since this area 40A is mechanically coupled to the object 80 via the adhesive 82. The second area 40B, since it has no direct mechanical coupling to the object 80, may be operable to only measure the temperature of the object 80. In another embodiment, a second adhesive (not shown) may be placed beneath the second area 40B (in addition to the adhesive 82 as shown). With respect to the physical property measured by the first area 40A, the adhesive 82 may have a higher level of transmittance than the second adhesive such that the first area 40A is more strongly affected by the physical property than the second area 40B, which is still operable to measure another physical property. In this case, the subsequent signal processing unit may separate these effects so that both physical properties can be determined.

In yet another embodiment, the SAW device may produce (in addition to the one or more reference/measure pairs) an identification signal for identifying the wireless sensor. The identification signal may be derived from the RF interrogation signal and may be delayed by a third time delay. The measuring system may receive the identification signal and compare it in the time domain to the reference signal. Based on this comparison, the measuring system may be able to identify the sensor. Employing an identification signal may be used when multiple wireless sensors are present in the same multi-path clutter environment and may help the measuring system determine which wireless sensor is responding to the RF interrogation signal.

With regard to the SAW device, the identification signal may be produced by placing one or more identification reflectors on the SAW device. These may be placed at a location on the SAW device such that the reference/measurement pair and the identification signal do not interfere with each other in the time domain. The identification reflectors may be placed such that the identification signal comprises a series of RF pulses which are spaced apart at a known time interval and may represent binary digits. For example, the SAW device may have four identification reflectors which produce an identification signal having four RF pulses which are spaced apart at 10 nanoseconds. The measuring system may interpret these four RF pulses as the binary number "1111," which is the number 15 in decimal. In another example, the SAW device from the previous example may lack the third identification reflector. Thus, this arrangement may produce three RF pulses, the first two of which are spaced at 10 nanoseconds, and the last two of which are spaced at 20 nanoseconds. The measuring system may interpret these three RF pulses as the binary number 1101, which is the number 13 in decimal. In doing so, the measuring system may interpret the absence of an RF signal 10 nanoseconds after the second RF pulse as a binary zero. Many variations of producing and measuring an identification signal may be used, as is known in the art.

Because the RF interrogation signal is transmitted in a multi-path clutter environment, the RF interrogation signal may reflect off the reflecting structures. Many of these reflected signals may be returned to the transponder without having reached the wireless sensor. These reflected signals eventually decay since some energy of the signal is lost at each point of reflection. As previously discussed herein, this process is called multi-path ringdown. As an illustrative example, a 2.5 GHz interrogation signal may require approximately 15 nanoseconds to decay when the measuring system is disposed in an operating jet aircraft engine.

During the multi-path ringdown, many of these reflected RF interrogation signals may be received by the transponder. As a result, during this time, it may be more difficult for the transponder to distinguish between the decaying RF interrogation signals and the reference and measurement signals. Consequently, the wireless sensor may be designed such that the time delay introduced into the reference signal and the measurement signal may be longer than the multi-path ringdown time. In such a case, the multi-path ringdown will not interfere with the reception of the reference signal or the measurement signal.

As previously indicated, the use of two different time delays on the same SAW device permits a reference signal and a measurement signal to be retransmitted to the transponder. The amount of time between the reference signal and measurement signal may be called the sensor delay. Since the sensor delay may be very short (e.g., 100 nanoseconds or less), the geometry of the propagation environment may not change significantly during that time, even in the case where the reflecting structures are moving very rapidly, such as in the compressor or turbine stage of a jet engine. Thus the sensor delay may not be affected by the multi-clutter propagation environment. The delays in the reference and measurement signals (with respect to the interrogation signal) overcome the multi-path ringdown problems of spurious reflection signals overlapping the desired data signals, and the sensor delay overcomes the problem of induced modulation of the propagating signals by the changing propagation environment due to the reflecting structures.

Figure 7:
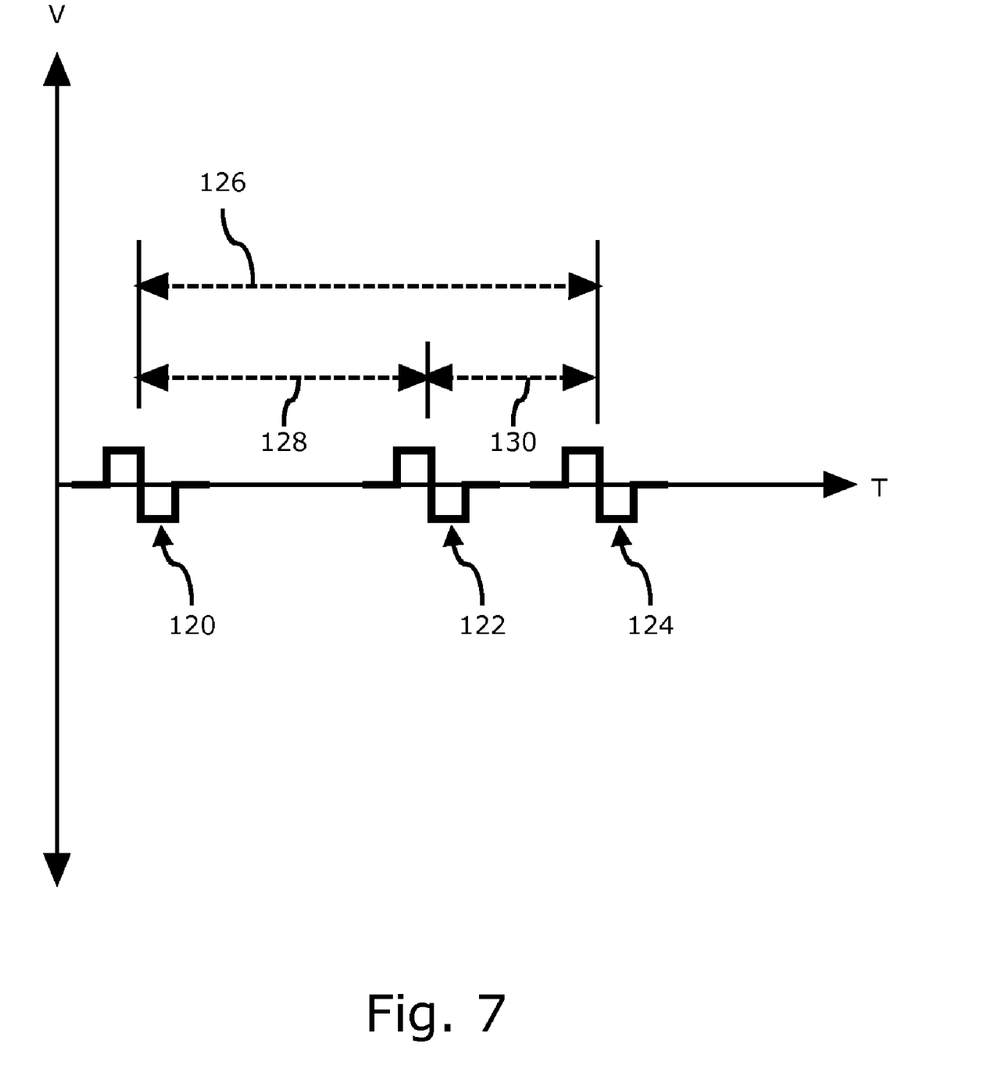
FIG. 7 depicts the temporal relationship between the RF interrogation signal, the reference signal, and the measurement signal according to one or more embodiments described herein.

Referring now to FIG. 7, the temporal relationship between the RF interrogation signal, the reference signal, and the measurement signal will now be discussed. To begin a measurement, an RF interrogation signal 120 is sent by the transponder to the wireless sensor. As discussed above, the wireless sensor responds with a reference signal 122 and a measurement signal 124, both of which are delayed in time. The reference signal 122 is delayed from the RF interrogation signal 120 by an amount of time referred to as a reference delay 128. The measurement signal 124 is likewise delayed from the RF interrogation signal 120 by an amount of time referred to as a measurement delay 126. As previously discussed, the reference delay 128 and the measurement delay 126 may be longer than the multi-path ringdown time caused by the RF interrogation signal 120. The transponder may receive the reference signal 122 and the measurement signal 124 and communicate them to the signal processing unit. The signal processing unit may compare the reference signal 122 and the measurement signal 124 in the time domain. This time-domain measurement may determine the sensor delay 130 between the reference signal 122 and the measurement signal 124. This sensor delay 130 may be received by the transponder and determined by the signal processing unit.

Although the signals (i.e., 120, 122, 124) shown in FIG. 7 are depicted as square waves, they may actually be bursts of sinusoids or other waveforms having a frequency determined by the interrogation signal. More specifically, it is contemplated that the signals may be deterministic, random, or pseudo-random. In many cases, the signals will be relatively complex waveforms modulated to fit a particular diagnostic purpose. In one embodiment, the signal processing unit measures the time delay by, for example, using the sinusoid (within a particular burst) with the largest amplitude. Other techniques may be used to measure the time delay as is known in the art. Furthermore, in order to improve accuracy, the signal processing unit may also measure the phase shift as one component of the time delay.

Referring back to FIG. 1, the signal processing unit 30 may be operable to receive the reference and measurement signals from the transponder 20. In one embodiment, the signal processing unit 30 may split reference signal from the measurement signal so as to delay one or both of the signal and correlated with each other by use of a microwave mixer and low pass filter. The resulting filtered signals may be sampled by an analog-to-digital converter and processed in the system computer (not shown). The mixer may have both in-phase and quadrature phase outputs so that the differential phase can be extracted using a mathematical arctangent in the post processing.

In another embodiment, the signal processing unit 30 receives and amplifies the reference and measurement signals. The amplified signals are input to a microwave quadrature mixer. High speed switches may be used to create the RF interrogation signal and prevent it from interfering with the received signals. A microwave splitter is used to provide a reference (or local oscillator) signal to the quadrature mixer. The outputs of the quadrature mixer can be filtered, for example, with a low pass filter with a cutoff frequency of 20 MHz or less. The in-phase and the quadrature phase signals are fed to the analog-to-digital converter, which converts these signals into a digital format capable of being further processed by a computer (not shown).

These are only two exemplary embodiments of the signal processing unit. Many other variations of the signal processing unit are contemplated, as may be known to those skilled in the art.

In one contemplated embodiment, the wireless sensor is physically mounted to the blade of a compressor or turbine in a jet engine. The physical property measured may be the strain of the blade, the temperature of the blade, or some other physical property of the blade. The wireless sensor may be mounted to the blade using any one of a variety of mounting means including, but not limited to, conventional fasteners (e.g., screws or bolts) and adhesives.

In another embodiment, the wireless sensor may be physically mounted to one object while measuring a physical property of another object or a fluid. For example, it may be desirable to measure a physical property of the gas flowing by a blade of a compressor or turbine in a jet engine. The physical property measured may be the temperature of the gas, the chemical composition of the gas, or a partial pressure of a component of the gas mixture. Accordingly, the wireless sensor may be mounted to the blade while its location on the blade permits the sensor to be physically coupled, i.e., fluidly coupled, to the gas flowing by the blade. As a result, the sensor may be capable of measuring the appropriate physical property of the gas. Other physical properties may be measured as can be gleaned from the technical literature or yet-to-be-discovered technology.

In still another embodiment, the wireless sensor may be mounted to an object, such as a structural member, inside a tank or a pipe. The tank or pipe may contain a fluid which is physically coupled to the wireless sensor. Accordingly, the wireless sensor may be operable to measure a physical property of the fluid in the tank or pipe. For example, the wireless sensor may be operable to measure the temperature of the fluid inside the tank or pipe. As another example, the wireless sensor may be operable to measure a chemical composition of the fluid. Other physical properties of the fluid may be also measured, as is known in the art.

In yet another embodiment, the wireless sensor may simply "float" in a fluid whose physical property is being measured. That is, one or more wireless sensors may be added to the fluid and may remain suspended in the fluid while operating. In this embodiment, the sensors are not physically mounted to anything, and their location within the fluid may depend on a number of factors, including but not limited to the weight of the sensor, whether the fluid is moving, and the specific gravity of the fluid. For example, one or more wireless sensors may be added to a fluid located in a holding tank and may sense the temperature of the fluid. As such, the sensors may float randomly within the tank. A filter, located at the outlet of the tank, may prevent the sensors from leaving the tank when the fluid is removed.

When sensing the physical property of a fluid (e.g., a gas or a liquid), the wireless sensor may be operable to measure a number of physical properties, including but not limited to a temperature of the fluid, a velocity of the fluid, a flow direction of the fluid, a pressure of the fluid, a nuclear characteristic of the fluid, an acoustic characteristic of the fluid, a chemical composition of the fluid, a pH factor of the fluid, a dielectric property of the fluid, a density of the fluid, a particle distribution of the fluid, a magnetic property of the fluid, an electrical property of the fluid, or a light absorption property of the fluid. When the wireless sensor is measuring the physical property of a gas, it may additionally determine a species of the gas or a humidity of the gas. When the wireless sensor is measuring the physical property of a liquid, it may additionally determine the viscosity of the liquid. Other physical properties of fluids (both gases and liquids) may be measured as well, as is known in the art. For example, a wireless sensor may be mounted to a blade of a compressor or turbine in a jet engine, and the blade is positioned in a gas flowing through the compressor or turbine. In this case, the comparison of the retransmitted reference signal and the retransmitted measurement signal (from the wireless sensor) may be used to determine an unknown physical property of the gas. In another example, a wireless sensor may be mounted to an object inside a tank or a pipe containing the fluid. In this case, the comparison of the retransmitted reference signal and the retransmitted measurement signal (from the wireless sensor) may be used to determine the unknown physical property of the fluid.

When sensing the physical property of an object, the wireless sensor may be operable to measure a number of physical properties, including but not limited to a temperature of the object, a stress or a strain of the object, a torque characteristic of the object, an acoustic characteristic of the object, a chemical composition of the object, a nuclear characteristic of the object, a dielectric property of the object, a magnetic property of the object, an electrical property of the object, or a light absorption property of the object. For example, the wireless sensor may be mounted to a blade of a compressor or turbine in a jet engine; a part of a helicopter blade mechanism; a shaft of a helicopter main rotor or tail rotor; a gear, a gear tooth, or a gear carrier in a transmission; or a rotating or translating machinery or a link in a kinematic mechanism. When mounted as such, the comparison of the retransmitted reference signal and the retransmitted measurement signal (from the wireless sensor) may be used to determine an unknown physical property of the object to which the wireless sensor is mounted, such as mechanical stress or temperature.

In still another embodiment, the wireless sensor may be mounted to an object on which the wireless sensor is operable to measure the thickness of a material placed on the object or accumulated on the object. For example, the wireless sensor may be operable to measure the thickness of ice, rust, a biological material, or a protective coating which accumulates or is placed on the object.

For the purposes of describing and defining the present invention, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is further noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present invention or to emphasize alternative or additional features that may or may not be utilized in a particular embodiment of the present invention.

For the purposes of describing and defining the present invention it is noted that the term "approximately" is utilized herein to represent the inherent degree of uncertainty that may be attributed to any quantitative comparison, value, measurement, or other representation. For example, it is stated that the multi-path ringdown time may be approximately 15 nanoseconds for a 2.5 GHz interrogation pulse. Because the ringdown may be exponential and may depend on the location and number of reflecting structures (some of which may be moving), the point in time at which the ringdown is considered complete may vary to some degree.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A method for determining an unknown physical property of an object or fluid in a dynamic multi-path clutter environment, the method comprising:
    transmitting an RF interrogation signal to a wireless sensor physically coupled to the object or the fluid in the dynamic multi-path clutter environment wherein the transmitted RF interrogation signal generates multipath ringdown signals in the dynamic multi-path clutter environment;
    receiving a retransmitted reference signal and a retransmitted measurement signal from the wireless sensor, wherein the structure of the wireless sensor is such that, upon receipt of the RF interrogation signal, the wireless sensor produces a reference signal and a measurement signal and retransmits the reference signal and the measurement signal in the dynamic multi-path clutter environment, and wherein
        the retransmitted reference signal and the retransmitted measurement signal are derived from the RF interrogation signal,
        the retransmitted reference signal is delayed by a first time delay,
        the retransmitted measurement signal is delayed by a second time delay that is a function of the unknown physical property,
        the first and second time delays are associated by a known relationship defined by the wireless sensor and are each long enough to permit retransmission of the reference and measurement signals without substantial overlap in time with the multipath ringdown signals generated by the RF interrogation signal, and
        the first and second time delays are such that a time period between retransmission of the reference signal and the measurement signal is sufficiently short to minimize data burst calibration errors due to the dynamics of the multi-path clutter environment;
    using a comparison of the retransmitted reference signal and the retransmitted measurement signal in the time domain to determine the unknown physical property of the object or fluid.

2. The method of claim 1 wherein the first and second time delays are each long enough to permit retransmission of the reference and measurement signals at least approximately 20 ns after transmission of the RF interrogation signal.

3. The method of claim 1 wherein the first and second time delays are such that a time period between retransmission of the reference signal and the measurement signal is less than approximately 1,000 ns.

4. The method of claim 1 wherein:
    the RF interrogation signal is transmitted to a wireless sensor mounted to a blade of a compressor or turbine in a jet engine stage comprising a plurality of blades in a gas flowing through the compressor or turbine in the engine stage;
    the engine stage is characterized by an operating range encompassing a rotation rate of approximately 20,000 rpm;
    the first and second time delays are each long enough to permit retransmission of the reference and measurement signals at least approximately 20 ns after transmission of the RF interrogation signal;
    the first and second time delays are such that a time period between retransmission of the reference signal and the measurement signal is less than the time it would take a selected blade of the jet engine stage to pass a given degree of rotation at a rotation rate of approximately 20,000 rpm; and the comparison of the retransmitted reference signal and the retransmitted measurement signal is used to determine an unknown physical property of the blade to which the wireless sensor is mounted or the gas flowing through the compressor or turbine.

5. The method of claim 1 wherein the wireless sensor is configured such that the first time delay is also a function of the unknown physical property.

6. The method of claim 1 wherein the wireless sensor is configured such that the first time delay is independent of the unknown physical property.

7. The method of claim 1 wherein the wireless sensor is configured such that the first time delay and the second time delay are both functions of a peripheral physical property of the object or fluid.

8. The method of claim 7 wherein:
the wireless sensor comprises a base, an antenna, a power divider, a first SAW device, and a second SAW device;
the antenna, power divider, and SAW devices are mechanically coupled to the base;
either the base is physically coupled to the object or the first and second SAW devices are physically coupled to the fluid;
the first SAW device is in electrical communication with the power divider and is operable to produce the reference signal, produce the measurement signal, and communicate the reference signal and the measurement signal to the power divider;
the second SAW device is in electrical communication with the power divider and is operable to produce the additional reference signal, produce the additional measurement signal, and communicate the additional reference signal and the additional measurement signal to the power divider;
the power divider is in electrical communication with the antenna and is operable to communicate the RF interrogation signal from the antenna to the first and second SAW devices and communicate the measurement and reference signals from the first and second SAW devices to the antenna; and
the antenna is operable to receive the RF interrogation signal, communicate the RF interrogation signal to the power divider, receive signals from the power divider, and retransmit the signals received from the power divider in the dynamic multi-path clutter environment.

9. The method of claim 1 wherein:
a plurality of wireless sensors are physically coupled to an object or fluid in the dynamic multi-path clutter environment; and
individual ones of the plurality of wireless sensors are characterized by respective distinct signature resonant frequencies to enable identification of individual wireless sensors by reference to its signature resonant frequency.

10. The method of claim 1 wherein the wireless sensor is configured to produce and retransmit at least one additional reference signal and at least one additional measurement signal representative of a peripheral unknown physical property of the object, the fluid, a second object, or a second fluid, and the method additionally comprises:
receiving the additional retransmitted reference signal and the additional retransmitted measurement signal; and
using a comparison of the retransmitted reference signal and the retransmitted measurement signal in the time domain to determine the peripheral unknown physical property.

11. The method of claim 1 wherein the wireless sensor is configured to produce and retransmit at least one additional reference signal and at least one additional measurement signal representative of the unknown physical property of the object or fluid, and the method additionally comprises:
receiving the additional retransmitted reference signal and the additional retransmitted measurement signal; and
using a comparison of the retransmitted reference signal and the retransmitted measurement signal in the time domain to determine a gradient of the unknown physical property.

12. The method of claim 1 wherein the comparison of the retransmitted reference signal and the retransmitted measurement signal is used to determine a state of matter of the object or the fluid.

13. The method of claim 1 wherein the RF interrogation signal is transmitted to a wireless sensor suspended in a fluid or mounted to an object positioned in a fluid, and the comparison of the retransmitted reference signal and the retransmitted measurement signal is used to determine the unknown physical property of the fluid.

14. The method of claim 13 wherein the fluid is a gas and the comparison of the retransmitted reference signal and the retransmitted measurement signal is used to determine a species of the gas.

15. The method of claim 13 wherein the fluid is a gas mixture and the comparison of the retransmitted reference signal and the retransmitted measurement signal is used to determine the composition of the gas mixture or a partial pressure of a component of the gas mixture.

16. The method of claim 13 wherein the RF interrogation signal is transmitted to a wireless sensor mounted to a blade of a compressor or turbine in a jet engine, the blade is positioned in a gas flowing through the compressor or turbine, and the comparison of the retransmitted reference signal and the retransmitted measurement signal is used to determine an unknown physical property of the gas.

17. The method of claim 1 wherein the RF interrogation signal is transmitted to a wireless sensor mounted to an object inside a tank or a pipe containing the fluid, and the comparison of the retransmitted reference signal and the retransmitted measurement signal is used to determine the unknown physical property of the fluid.

18. The method of claim 1 wherein the RF interrogation signal is transmitted to a wireless sensor mounted to an object, and the comparison of the retransmitted reference signal and the retransmitted measurement signal is used to determine a mechanical stress or a temperature of the object to which the sensor is mounted.

19. The method of claim 1 wherein the RF interrogation signal is transmitted to a wireless sensor mounted to an object, and the comparison of the retransmitted reference signal and the retransmitted measurement signal is used to determine a thickness of a material placed on the object or accumulated on the object.

20. A system for determining an unknown physical property of an object or a fluid in a dynamic multi-path clutter environment, the system comprising a transponder, a wireless sensor, and a signal processing unit, wherein:
the transponder is operable to transmit an RF interrogation signal to the wireless sensor physically coupled to the object or the fluid in the dynamic multi-path clutter environment wherein the transmitted RF interrogation signal generates multipath ringdown signals in the dynamic multi-path clutter environment;

the transponder is further operable to receive a retransmitted reference signal and a retransmitted measurement signal from the wireless sensor in the dynamic multi-path clutter environment, produce a reference signal and a measurement signal, and retransmit the reference signal and the measurement signal in the dynamic multi-path clutter environment;

the reference signal and measurement signal are derived from the RF interrogation signal;

the reference signal is delayed by a first time delay;

the measurement signal is delayed by a second time delay that is a function of the unknown physical property;

the first and second time delays are associated by a known relationship defined by the wireless sensor and are each long enough to permit retransmission of the reference and measurement signals without substantial overlap in time with the multipath ringdown signals generated by the RF interrogation signal;

the first and second time delays are such that a time period between retransmission of the reference signal and the measurement signal is sufficiently short to minimize data burst calibration errors due to the dynamics of the multi-path clutter environment; and the signal processing unit is electrically coupled to the transponder and is operable to compare the reference signal and the measurement signal in the time domain and, using this comparison, determine the unknown physical property of the object or the fluid.

* * * * *